(12) United States Patent
Cottam et al.

(10) Patent No.: US 8,124,654 B2
(45) Date of Patent: Feb. 28, 2012

(54) DERIVATIVES OF HYPOESTOXIDE AND RELATED COMPOUNDS

(75) Inventors: Howard B. Cottam, Escondido, CA (US); Emmanuel A. Ojo-Amaize, Fontana, CA (US); Emeka J. Nchekwube, Morgan Hill, CA (US); Olusola A. Oyemade, Rancho Cucamonga, CA (US); Donna G. Nchekwube, Morgan Hill, CA (US)

(73) Assignee: Immune Modulation, Inc., Bloomington, CA (US)

( * ) Notice: Subject to any disclaimer, the term of this patent is extended or adjusted under 35 U.S.C. 154(b) by 247 days.

(21) Appl. No.: 12/268,910

(22) Filed: Nov. 11, 2008

(65) Prior Publication Data

US 2010/0120853 A1   May 13, 2010

(51) Int. Cl.
*A61K 31/335*   (2006.01)
*A61K 9/48*   (2006.01)
*A61K 9/52*   (2006.01)
*A61K 9/58*   (2006.01)
*A61K 36/00*   (2006.01)

(52) U.S. Cl. ........ 514/475; 424/451; 424/454; 424/457; 424/462; 424/725

(58) Field of Classification Search .................. 514/475; 424/451, 454, 457, 462, 725
See application file for complete search history.

(56) References Cited

U.S. PATENT DOCUMENTS

| 4,938,949 A | 7/1990 | Borch et al. |
| 5,801,193 A | 9/1998 | Ojo-Amaize et al. |
| 5,994,328 A | 11/1999 | Ojo-Amaize et al. |
| 6,001,871 A | 12/1999 | Ojo-Amaize et al. |
| 6,242,484 B1 | 6/2001 | Ojo-Amaize et al. |

FOREIGN PATENT DOCUMENTS

| WO | WO 98/46222 | 10/1998 |
| WO | WO 01/01975 | 1/2001 |

OTHER PUBLICATIONS

Akinbo et al. "Roseatoxide and dihypoestoxide: additional new diterpenoids from Hypoestes rosea," J. Natural Products, 1984, vol. 47, No. 2, pp. 308-311.*
Experimental Parasitology, Plasmodium berghei: Antiparasitic effects of orally administered Hypoestoxide in mice, vol. 117, No. 2, Aug. 29, 2007, Ojo-Amaize, et al., pp. 218-221.
International Search Report dated Aug. 21, 2009, International application No. PCT/US2008/012708 filed Nov. 13, 2008, 3 pages.

* cited by examiner

*Primary Examiner* — Shengjun Wang
(74) *Attorney, Agent, or Firm* — Pillsbury Winthrop Shaw Pittman LLP

(57) ABSTRACT

Novel diterpene compounds, in particular, hypoestoxide-related compounds, are provided in pure form or as contained in the native plant source, for treatment and prophylaxis of cancer, inflammatory diseases, hyperlipidemias, malaria, and diabetes mellitus. Embodiments also pertain to methods for using the hypoestoxide-related compounds to treat various diseases and symptoms associated with those diseases.

19 Claims, No Drawings

DERIVATIVES OF HYPOESTOXIDE AND RELATED COMPOUNDS

CROSS REFERENCE TO RELATED APPLICATIONS

Expressly incorporated herein by reference are U.S. Pat. Nos. 5,801,193, 5,994,328, 6,001,871 and 6,242,484, PCT WO 98/46222 and previously application, U.S. Ser. No. 09/298,653, now abandoned.

BACKGROUND OF THE INVENTION

Field of the Invention

This invention relates to the discovery, characterization and use of novel diterpene compounds, in particular, hypoestoxides, derivatives and related compounds, whether in pure form or contained in the native plant source, for treatment and prophylaxis of cancer, inflammatory diseases, hyperlipidemias, malaria, and diabetes mellitus. In addition, the compounds of the invention may be used in combination with other therapeutic agents known to be effective for the treatment and prevention of these conditions. Furthermore, compounds of the invention may be used as a component in a medical device, such as a drug eluting stent, for example, for use in prevention of cardiovascular restenosis following stent placement.

SUMMARY OF THE INVENTION

The present invention provides a description of novel compounds and methods of treating a host, such as a human, suffering from cancer, inflammatory diseases (including atherosclerosis), hyperlipidemias, malaria, or diabetes mellitus, or for use as a component in a medical device, such as a drug eluting stent, with hypoestoxides, derivatives and related compounds, whether in pure form or contained in the native plant source, that such pathological condition(s) is ameliorated thereby. Reference compound, hypoestoxide, is shown below for chemical naming purposes:

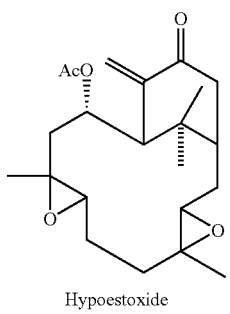

Hypoestoxide

In addition, methods of prophylaxis against the development of these conditions are provided. Thus, the method comprises administering to the afflicted host a therapeutically, or prophylactically, effective amount of the following compounds of formula I-IV:

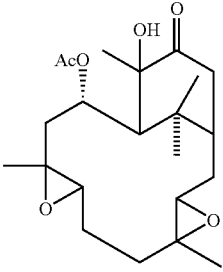

12-hydroxydihydrohypoestoxide

Formula I

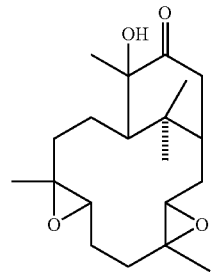

10-deacetoxy-12-hydroxydihydrohypoestoxide

Formula II

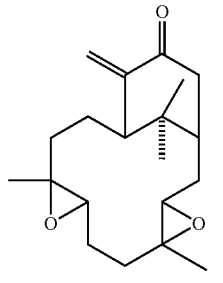

10-deacetoxyhypoestoxide

Formula III

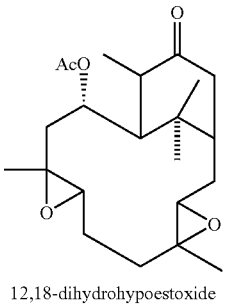

12,18-dihydrohypoestoxide

Formula IV and mixtures thereof, wherein the effective amount is sufficient to ameliorate at least one symptom of said disease(s), and compounds may be used alone or in combination with other agents useful for treatment of said disease(s). For example, there is provided a method for treating malaria in a host by administering to the host an effective amount of one or a mixture of the above compounds in which the effective amount is sufficient to provide prophylaxis of malaria or reduce malaria parasite development. These novel hypoestoxide-related compounds may be used in pure form or contained within the native plant source such as is found in the herb *Hypoestes rosea*. Finally, it is recognized that the compounds described here may be used in combination with other drugs useful to treat or prevent these diseases and/or conditions, such as other chemotherapeutic agents for cancer, other anti-parasitic agents for malaria, and other anti-inflammatory agents for inflammatory conditions.

Moreover, the compound of Formula IV, the reduced hypoestoxide, may be used to treat diseases differently than the parent hypoestoxide. Namely, this reduced compound was unexpectedly found to be much more potent against certain diseases and/or conditions. For example, Formula IV was unexpectedly found to be much more potent against malaria than any compound heretofore discovered in this class of natural products (see Example 1). Conversely, this same compound is not expected to possess anti-inflammatory activity to any great extent. Thus, the bioactivity profile of the reduced compound differs significantly from that of the other new compounds in the hypoestoxide class, including hypoestoxide itself. The other novel compounds represented by Formulas I, II and III are expected to be only about 25% similar in bioactivity to hypoestoxide as Formulas I-III do not inhibit IL-1β, IL-12 or TNF-αproduction. Conversely, hypoestoxide inhibits all the pro-inflammatory cytokines, IL-1β, IL-6, IL-12 and TNF-α respectively.

As used herein, the term "host" or "subject" is taken to mean human, as well as other animals. The term "ameliorate" means to improve, lessen the severity of or mitigate. The term "inflammatory diseases" is taken to mean any condition, whether acute or chronic, immune or non-immune, where inflammation is a key component, such as, but not limited to: arthritis, systemic lupus erythematosus (SLE), atherosclerosis, polymyositis, arteritis, acne, and psoriasis.

DETAILED DESCRIPTION OF THE INVENTION

Novel compounds of formula I-IV are described and have been characterized by standard chemical methods known in the art, such as ultraviolet spectrophotometry, mass spectrometry, nuclear magnetic resonance spectroscopy, and the like. Compounds of formula I-III are isolated from the extract of the shrub *Hypoestes rosea* while compound of formula IV is prepared from pure hypoestoxide by catalytic hydrogenation using a palladium catalyst.

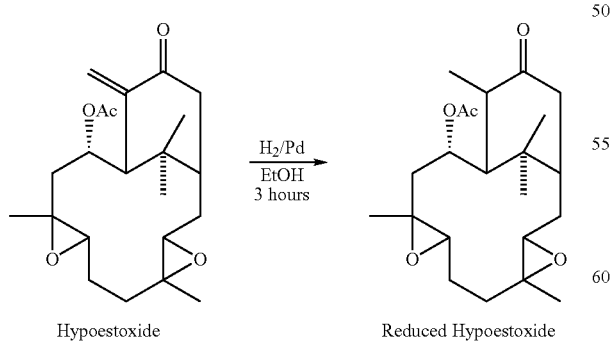

Thus, the present embodiments provide a composition for treating or reducing an inflammatory condition in a host, comprising administering to the host an effective amount of a compound having a formula selected from the group consisting of:

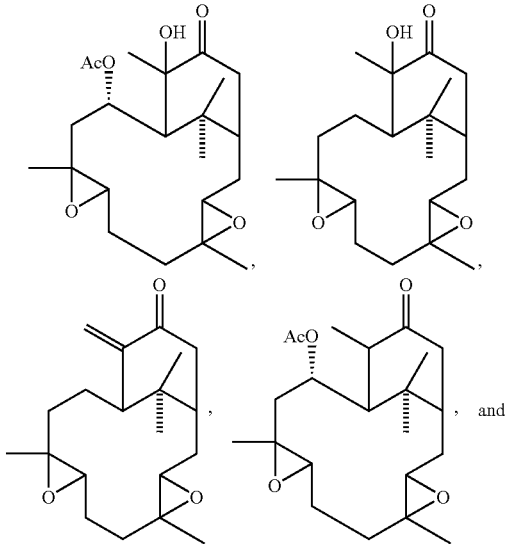

and mixtures thereof.

Also provided are methods of treating a host suffering from cancer, inflammatory diseases (including atherosclerosis), hyperlipidemias, malaria, or diabetes mellitus with the novel compounds, or of using the novel compounds as a component in a medical device, such as a drug eluting stent. In the subject methods, an effective amount of an agent as described above is administered in an amount sufficient to ameliorate at least one condition or symptom related to or associated with diseases such as: cancer, inflammatory diseases (including atherosclerosis), hyperlipidemias, malaria, or diabetes mellitus. A specific embodiment provides a method of reduction or treatment of an inflammatory condition in a host, comprising administering to the host an effective amount of a compound having a formula selected from the group consisting of:

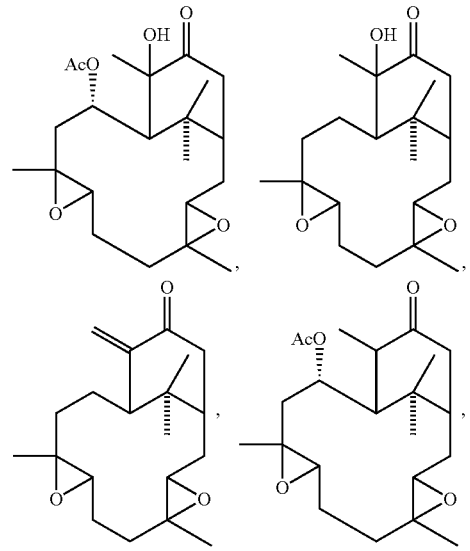

and mixtures thereof.

Also provided are methods of treating a host suffering from cancer, inflammatory diseases (including atherosclerosis and hyperlipidemias), malaria, or diabetes mellitus with the novel compounds, or of using the novel compounds as a component in a medical device, such as a drug eluting stent. In the subject methods, an effective amount of an agent as described above is administered in an amount sufficient to ameliorate at least one condition or symptom related to or associated with diseases such as: cancer, inflammatory diseases (including atherosclerosis and hyperlipidemias), malaria, or diabetes mellitus. A specific embodiment provides a method of reduction or treatment of an inflammatory condition in a host, comprising administering to the host an effective amount of a compound having a formula selected from the group consisting of:

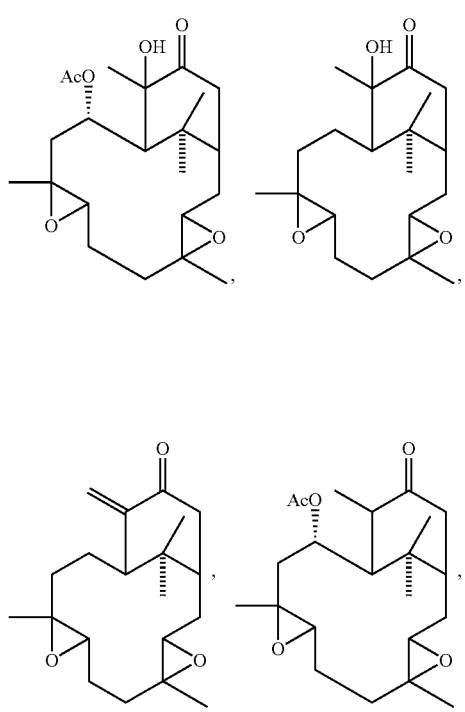

and mixtures thereof.

In embodiments, the method may administer an effective amount of the compounds for use as a component in a medical device, such as a drug eluting stent. For example, the compound may be coated on an intravascular stent and delivered to a vascular lumen of a host suffering from restenosis. In certain embodiments, the intravascular stent is coated with the compound in an effective amount of from about 0.1 micrograms to about 1000 micrograms. A chemotherapeutic agent and other such agents useful for treating the specific disease may be also coated on the stent. The stent may be coated by various methods, such as, coating by vapor deposition.

Also provided are methods for prophylactically treating a patient at risk of any of these conditions, such as in obese and genetically predisposed individuals, with an agent as described above, alone or in combination with standard chemotherapeutic agents, such as, Cyclosporin A, tacrolimus, and mixtures thereof, and the like. The present embodiments provide a method comprising administering to the afflicted host a therapeutically, or prophylactically, effective amount of a compound of formula I-IV:

Formula I

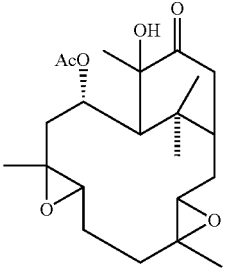

12-hydroxydihydrohypoestoxide

Formula II

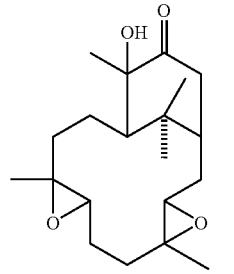

10-deacetoxy-12-hydroxydihydrohypoestoxide

Formula III

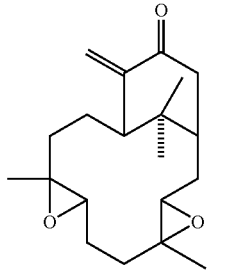

10-deacetoxyhypoestoxide

Formula IV

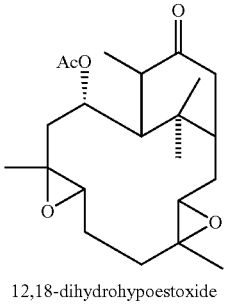

12,18-dihydrohypoestoxide

I and mixtures thereof.

The magnitude of a prophylactic or therapeutic dose of compounds of formula I-IV in the treatment or prevention of cancer, inflammatory diseases (including atherosclerosis and hyperlipidemias), malaria, or diabetes mellitus, or for use as a component in a medical device, such as a drug eluting stent, will vary with the progression of the disease, the chemotherapeutic agent(s) or other therapy used, and the route of administration. Generally, in cases where the disease has already progressed into later stages, a larger dose of the compounds may be needed.

In embodiments, trend dosages for cancer, around 5 mg/kg for a specific embodiment, are more than that for all the other indications. For example, the dosages for treating malaria can be around 250 micrograms per kilogram. All other dosages for the various indications discussed herein fall between these two exemplary embodiments. The dose, and the dose frequency, will also vary according to the age, body weight, and response of the individual patient. In general, the total daily dose range for compounds of formula I-IV, for the conditions described herein, is from about 0.1 mg to about 5000 mg, in single or divided doses. Preferably, a daily dose range should be about 1 mg to about 4000 mg, in single or divided doses. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response, for example, when the condition or symptom to be treated is ameliorated. The terms "an effective amount" are encompassed by the above-described dosage amounts, dose frequency schedule, and experimental data disclosed herein.

Any suitable route of administration may be employed for providing the patient with an effective dosage of compounds of formula I-IV. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The compound may be administered prior to, concurrently with, or after administration of other chemotherapy. The compound may also be administered continuously, e.g., in daily doses, during all or part of, a chemotherapy regimen, such as with insulin sensitizers or secretagogues. The compound, in some cases, may be combined with the same carrier or vehicle used to deliver the other chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may be from about 2% to about 60% by weight of the total weight of a given unit dosage form. The amount of active compound in such therapeutically or prophylactically useful compositions is such that an effective dosage level will be obtained.

In embodiments, the tablets, troches, pills, capsules, and the like may also contain the following: binders such as gum tragacanth, acacia, corn starch or gelatin; excipients such as dicalcium phosphate; a disintegrated agent such as corn starch, potato starch, alginic acid and the like; a lubricant such as magnesium stearate; and/or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. Prolonged absorption of the injectable compositions can be brought about by the use in the compositions of agents delaying absorption, such as, for example, aluminum monostearate and gelatin.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In the embodiments, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained in different manners, such as, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I-IV can be determined by comparing their in vivo activity in animal models. Methods for the extrapolation of effective dosages in mice, and other animals, to humans are known in the art; for example, see U.S. Pat. No. 4,938,949, which is hereby incorporated by reference.

All publications, patents, and patent documents are incorporated by reference herein, as though individually incorporated by reference. While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Parasite cultures were exposed to different concentrations of Formula IV or hypoestoxide (from 100× stocks in DMSO) for 48 h, beginning at the ring stage. Concentrations yielding 50% inhibition ($IC_{50}$) were extrapolated from plots of mean percent negative control activity over inhibitor concentration as measured by the uptake of $^3$H-hypoxanthine. Data was analyzed after logarithmic transformation and expressed as the geometric mean $IC_{50}$ and 95% confidence intervals.

Table 1 shows the in vitro effect of Formula IV (12,18-dihydrohypoestoxide on Malaria parasite development.

TABLE 1

| Drug | CQ-Resistant (W2 MR4) ($IC_{50}$ μM) | CQ-Sensitive (3D7) ($IC_{50}$ μM) |
|---|---|---|
| Hypoestoxide | 10.6 | 10.0 |
| Formula IV | 0.12 | 1.4 |

As seen in the table 1 above, the parent drug, hypoestoxide is weakly active against both chloroquine (CQ)-resistant and CQ-sensitive strains of *P. falciparum* malaria parasite. However, following modification of hypoestoxide into Formula IV, the modified Formula IV is 88 times more active than the parent hypoestoxide against the CQ-resistant malaria parasite strain, and about 7 times more active against the CQ-sensitive strain. The modification of hypoestoxide into 12,18-dihydro-hypoestoxide (Formula IV) to achieve potent activity against both CQ-resistant and CQ-sensitive strains of the malaria parasite demonstrates unexpected results. Other anti-parasitic agents such as sesquiterpene artemisinin, chloroquine, mixtures thereof, and the like, can also be administered in appropriate doses along with the compounds of formula I-IV.

Example 2

Five female mice per group were infected i.p. with $1 \times 10^5$ *P. berghei berghei* (EI strain) parasitized RBCs and 3 days later, oral therapy was started at 5 mg/Kg once daily with either Formula IV or Chloroquine for 3 days. Four days post infection, blood parasitemia was evaluated on each mouse on Giemsa-stained smears.

Table 2 shows the in vivo effect of Formula IV (12,18-dihydrohypoestoxide in Malaria-infected mice.

TABLE 2

| Drug (mg/Kg) | No. of mice | Reduction of Parasitemia (%) |
|---|---|---|
| Negative Control (Vehicle: DMSO/Water) | 5 | 0 |
| Positive Control (Chloroquine: 5 mg/Kg) | 5 | 96 |
| Formula IV (5 mg/Kg) | 5 | 92 |

Table 2 shows that Formula IV is effective in vivo in reducing parasitemia in the blood of malaria-infected mice. The result is comparable to that of chloroquine, a standard antimalarial drug.

Example 3

$1 \times 10^5$ melanoma cells were injected intravenously into the lateral tail vein of each of 30 mice. Before treatment, mice were randomized into six groups of 5 mice per group. Treatment began one hour after intravenous inoculation of the tumor cells. Drugs, at 5 mg/Kg were administered via oral route, once daily for 10 days. Treatment was stopped on day 10. On day 16, lungs were removed and fixed in 10% formaldehyde. The surface melanoma colonies were counted for each lung and the means were established for each group. The mean for each group was used to calculate % inhibition based on the vehicle control.

TABLE 3

| Drug (mg/Kg0 | No. of mice | Inhibition (%) |
|---|---|---|
| Vehicle (PBS) | 5 | 0 |
| Hypoestoxide (5 mg/Kg) | 5 | 70 |
| Formula I (5 mg/Kg) | 5 | 60 |
| Formula II (5 mg/Kg) | 5 | 70 |
| Formula III (5 mg/Kg) | 5 | 63 |
| Formula IV (5 mg/Kg) | 5 | 65 |

Table 3 shows the inhibition of lung colonization of $B16F_1$ melanocytes by hypoestoxide-derivative and related compounds in C57BL/6 Mice inoculated with melanoma cancer cells.

As can be seen in Table 3, the hypoestoxide-derivative, Formula IV and the other related compounds (Formulas I-III) all resulted in marked reduction of lung metastatic colonies.

Example 4

Human peripheral blood macrophages were stimulated in culture with LPS for 24 h, either alone or in the presence of 10 μM of Formula I, II or hypoestoxide. At the end of 24-hour culture, supernatants were removed and tested for the presence of IL-6 by enzymne-linked immunosorbent assay. The amounts of IL-6 produced are reported in pg/ml in Table 4, which demonstrates inhibition of the production of the pro-inflammatory cytokine, IL-6, by hypoestoxide-related compounds.

TABLE 4

| Drug | IL-6 (pg/ml) | Inhibition (%) |
|---|---|---|
| LPS (stimulant 3 μg/ml) | 1200 | 0 |
| Formula I (10 μM) | 250 | 79 |
| Formula II (10 μM) | 300 | 75 |
| Hypoestoxide (10 μM) | 50 | 96 |

As can be seen, Table 4 shows the anti-inflammatory effects of Formula I and II as judged by their ability to inhibit Interleukin-6 (IL-6) production in LPS-stimulated human peripheral blood macrophages.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A composition for treating malaria in a host, consisting essentially of an effective amount of a compound having a formula selected from the group consisting of:

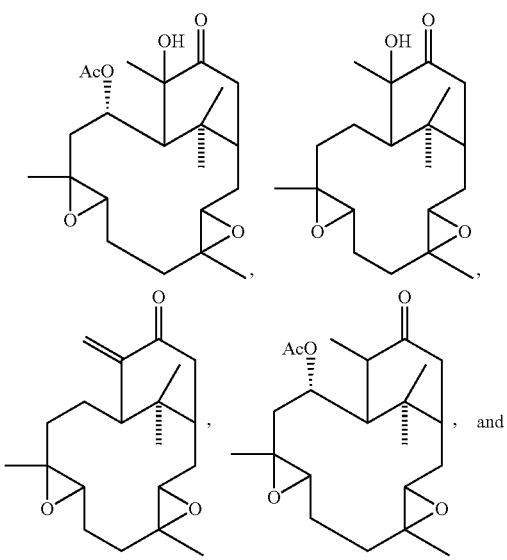

mixtures thereof, wherein the effective amount is sufficient to ameliorate at least one symptom of malaria.

2. The composition of claim 1 being active in reducing malaria parasite development.

3. The composition of claim 1 being present in a dosage form selected from the group consisting of a tablet, a troche, a dispersion, a suspension, a solution, a capsule, a patch, a syrup, an elixir and a wafer.

4. The composition of claim 1, wherein the compound is present in an amount of at least 0.1% by weight of a total weight of the composition.

5. A method for treating malaria in a host, comprising:
administering to the host an effective amount of a compound having a formula selected from the group consisting of:

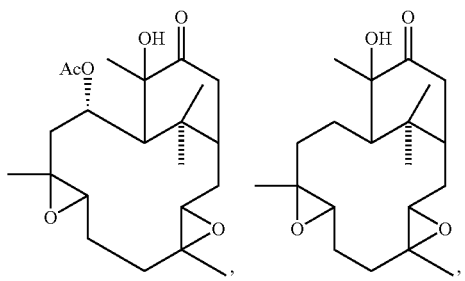

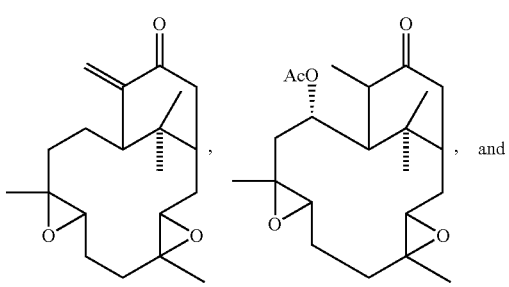

mixtures thereof, wherein the effective amount is sufficient to ameliorate at least one symptom of malaria; wherein the compound is in pure form.

6. The method of claim 5 further including monitoring the host for a reduction in a symptom associated with malaria.

7. The method of claim 5, wherein the compound is used in combination with other anti-parasitic agents.

8. The method of claim 7, wherein the other anti-parasitic agents are selected from the group consisting of sesquiterpene artemisinin, chloroquine, and mixtures thereof.

9. The method of claim 5, wherein the compound is active in reducing malaria parasite development.

10. The method of claim 5 further including incorporating the compound in a dosage form selected from the group consisting of a tablet, a troche, a dispersion, a suspension, a solution, a capsule, a patch, a syrup, an elixir and a wafer.

11. The method of claim 10, wherein the compound is administered in a dosage form further comprising a liquid carrier.

12. The method of claim 5, wherein the compound is administered in a daily dose range of from about 0.1 mg to about 5000 mg, in single or divided doses.

13. The method of claim 12, wherein the compound is administered in a daily dose range of from about 1.0 mg to about 4000 mg, in single or divided doses.

14. The method of claim 5, wherein the compound is present in an amount of at least 0.1% by weight of a total weight of a given unit dosage form.

15. The method of claim 14, wherein the compound is present in an amount of from about 2% to about 60% by weight of a total weight of a given unit dosage form.

16. The method of claim 5, wherein the compound is administered in a composition further comprising a binder, a disintegrated agent, a lubricant and a sweetening agent.

17. The method of claim 5 further including incorporating the compound into a sustained-release preparation or device.

18. A method for treating malaria in a host, comprising:

administering to the host an effective amount of a compound having a formula selected from the group consisting of:

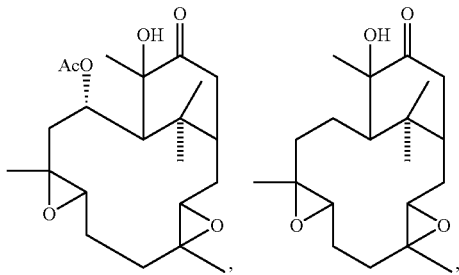

,

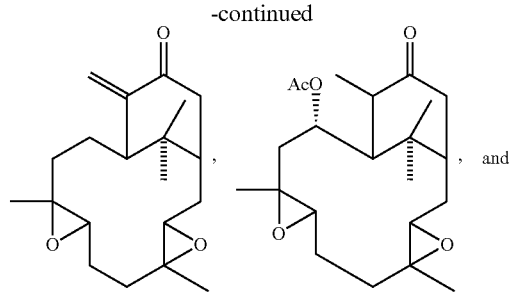

, and mixtures thereof, wherein the effective amount is sufficient to reduce malaria parasite development; wherein the compound is in pure form.

19. The method of claim 18, wherein the malaria parasite is selected from the group consisting of chloroquine-resistant *P. falciparum* malaria parasite, chloroquine-sensitive *P. falciparum* malaria parasite, and mixtures thereof.

* * * * *